US012312322B2

(12) United States Patent
Lee et al.

(10) Patent No.: US 12,312,322 B2
(45) Date of Patent: May 27, 2025

(54) DIOL COMPOUND, POLYCARBONATE, AND PREPARATION METHOD THEREOF

(71) Applicant: LG CHEM, LTD., Seoul (KR)

(72) Inventors: Dayoung Lee, Daejeon (KR); Ki Jae Lee, Daejeon (KR); Mooho Hong, Daejeon (KR); Young Young Hwang, Daejeon (KR); Youngwook Son, Daejeon (KR); Daehyeon Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 832 days.

(21) Appl. No.: 17/611,057

(22) PCT Filed: Sep. 3, 2020

(86) PCT No.: PCT/KR2020/011857
§ 371 (c)(1),
(2) Date: Nov. 12, 2021

(87) PCT Pub. No.: WO2021/045527
PCT Pub. Date: Mar. 11, 2021

(65) Prior Publication Data
US 2022/0251056 A1 Aug. 11, 2022

(30) Foreign Application Priority Data

Sep. 5, 2019 (KR) .................. 10-2019-0110305
Sep. 2, 2020 (KR) .................. 10-2020-0111774

(51) Int. Cl.
C08G 63/64 (2006.01)
C07D 307/68 (2006.01)
C07D 333/38 (2006.01)
C08G 64/08 (2006.01)
C08G 64/24 (2006.01)
C08G 64/30 (2006.01)

(52) U.S. Cl.
CPC ......... *C07D 307/68* (2013.01); *C07D 333/38* (2013.01); *C08G 63/64* (2013.01); *C08G 64/081* (2013.01); *C08G 64/24* (2013.01); *C08G 64/305* (2013.01)

(58) Field of Classification Search
CPC ......... C08L 67/02; C08L 69/00; C08G 63/06; C08G 63/64; C08G 64/305; C07D 307/68; C07D 333/38
See application file for complete search history.

(56) References Cited

U.S. PATENT DOCUMENTS

| 4,579,934 | A | * | 4/1986 | Brinkmeyer | .......... C08G 63/64 528/125 |
| 4,927,903 | A | | 5/1990 | Schreckenberg | |
| 5,510,455 | A | | 4/1996 | Hatke | |
| 6,300,456 | B1 | | 10/2001 | Musa | |
| 6,300,459 | B1 | | 10/2001 | Kaneko et al. | |
| 2008/0153810 | A1 | | 6/2008 | Ronsheim et al. | |
| 2009/0306100 | A1 | | 12/2009 | Barbosa et al. | |
| 2017/0283547 | A1 | | 10/2017 | Ko et al. | |
| 2017/0298177 | A1 | | 10/2017 | Lee et al. | |
| 2017/0321014 | A1 | | 11/2017 | Lee et al. | |
| 2018/0255975 | A1 | | 9/2018 | Kolar | |

FOREIGN PATENT DOCUMENTS

| CN | 106519200 B | 2/2019 | |
| EP | 0242278 A2 | 10/1987 | |
| EP | 3628699 A1 | 4/2020 | |
| JP | 2012-122023 A | 6/2012 | |
| JP | 2014-152210 A | 8/2014 | |
| KR | 100796634 B1 | 1/2008 | |
| KR | 10-2014-0017139 A | 2/2014 | |
| KR | 10-2016-0010939 A | 1/2016 | |
| KR | 10-2016-0026062 A | 3/2016 | |
| KR | 101678615 B1 | 11/2016 | |
| KR | 10-2017-0005363 A | 1/2017 | |
| KR | 10-2017-0027256 A | 3/2017 | |
| KR | 20190038161 A | 4/2019 | |
| KR | 10-2019-0079045 A | 7/2019 | |
| WO | 2008-061109 A2 | 5/2008 | |
| WO | 2008-067121 A2 | 6/2008 | |
| WO | WO-2012073970 A1 * | 6/2012 | ............. C08G 64/06 |
| WO | WO-2013092667 A1 * | 6/2013 | ........... C08G 63/605 |
| WO | 2019-156432 A1 | 8/2019 | |

OTHER PUBLICATIONS

Gomes et al Synthesis and Characterization of Poly(2,5-furan dicarboxylate)s Based on a Variety of Diols, Journal of Polymer Science Part A: Polymer Chemistry, vol. 49, 3759-3768 (2011), Published online Jun. 20, 2011.*
Choi et al Biomass-Derived Furanic Polycarbonates: Mild Synthesis and Control of the Glass Transition Temperature, Journal of Polymer Science, 2019, 57, 1796-1800, published online Jul. 29, 2019.*
Carolus H. R. M. Wilsens et al., "Aromatic thermotropic polyesters based on 2, 5-furandicarboxylic acid and vanillic acid," Polymer, vol. 55, No. 10, May 13, 2014, XP028650044, 2432-2439. (8 Pages).
Nguyen, et al. "The Quest For High Glass Transition Temperature Bioplastics", Journal of Materials Chemistry A, 2018, vol. 6, No. 20, DOI: 10.1039/c8ta00377g, 34 pages.
Wilsens, et al. "Thermotropic Polyesters from 2,5-Furandicarboxylic Acid and Vanillic Acid: Synthesis, Thermal Properties, Melt Behavior, and Mechanical Performance", Macromolecules, 2014, vol. 47, pp. 3306-3316.
Diao, et al. "Furan-Based Co-Polyesters With Enhanced Thermal Property: Poly(1,4-butylene-co-1,4-Cyclohexanedimethylene 2,5-Furandicarboxylic Acid)", RSC Adv., 2016, DOI: 10.1039/C5RA27617A, 29 pages.

(Continued)

*Primary Examiner* — Gregory Listvoyb
(74) *Attorney, Agent, or Firm* — Bryan Cave Leighton Paisner LLP

(57) ABSTRACT

Provided are a diol compound which may be used to prepare a polycarbonate having excellent weather resistance, hardness, heat resistance, transparency, impact resistance, etc. while having excellent mechanical properties, a polycarbonate prepared by using the same, and a preparation method thereof.

12 Claims, 8 Drawing Sheets

(56) References Cited

OTHER PUBLICATIONS

Chemical Abstract compound, STN express RN 507445-42-3 (Entered STN: Apr. 30, 2003).
Office Action for KR Patent Application 20190110301 dated Jan. 22, 2024.
Office Action for KR Patent Application 20190110303 dated Jan. 22, 2024.
Moore and Stupp "Synthesis of a Chemically Ordered Liquid Crystal Polymer," Macromolecules, vol. 21, No. 5, 1988 pp. 1217-1221.

* cited by examiner

DIOL COMPOUND, POLYCARBONATE, AND PREPARATION METHOD THEREOF

CROSS-REFERENCE TO RELATED APPLICATION

The present application is a National Phase entry pursuant to 35 U.S.C. § 371 of International Application No. PCT/KR2020/011857, filed on Sep. 3, 2020, and claims priority to and the benefit of Korean Patent Application Nos. 10-2019-0110305 and 10-2020-0111774, filed on Sep. 5, 2019 and Sep. 2, 2020, respectively, the disclosures of which are hereby incorporated herein by reference in their entirety for all purposes as if fully set forth herein.

TECHNICAL FIELD

The present invention relates to a diol compound, a polycarbonate, and a preparation method thereof. More specifically, the present invention relates to a diol compound which may be used to prepare a novel structure of a polycarbonate having improved weather resistance, hardness, heat resistance, impact resistance, etc. while having excellent mechanical properties, a polycarbonate prepared by using the same, and a preparation method thereof.

BACKGROUND

Polycarbonate resins have excellent impact strength, dimensional stability, heat resistance, transparency, etc., and thus the polycarbonate resins are polymeric materials having application in a wide range of uses, such as exterior materials of electrical and electronic products, automobile parts, building materials, optical components, etc.

As the application fields of these polycarbonate resins have recently expanded, such as being applied to glass and lenses, there is a need for the development of a novel structure of polycarbonate with improved weather resistance and refractive index while maintaining intrinsic properties of the polycarbonate resins.

Accordingly, studies have been attempted to obtain desired physical properties by copolymerizing two or more kinds of aromatic diols having different structures to introduce units having different structures into the main chain of polycarbonate. However, most technologies have limitations in that production costs are high, and when chemical resistance or impact strength increases, transparency decreases, and on the contrary, when the transparency increases, the chemical resistance or impact strength decreases.

Accordingly, there is still a need for research and development on a novel structure of polycarbonate, which has excellent weather resistance, heat resistance, transparency, hardness, and impact resistance while having excellent mechanical properties such as hardness, etc.

SUMMARY OF THE INVENTION

There is provided a diol compound which can be used to prepare a polycarbonate having improved weather resistance, hardness, heat resistance, and impact resistance while having excellent mechanical properties, a polycarbonate prepared by using the same, and a preparation method thereof.

There is provided a diol compound represented by Chemical Formula 1.

Further, there is provided a polycarbonate including the diol compound represented by Chemical Formula 1, a compound represented by Chemical Formula 2, and a carbonate precursor-derived repeating unit.

Further, there is provided a method of preparing a polycarbonate, the method including the step of polymerizing a composition including the diol compound represented by Chemical Formula 1, the compound represented by Chemical Formula 2, and the carbonate precursor.

Hereinafter, a diol compound, a polycarbonate, and a preparation method thereof according to specific embodiments of the present invention will be described in more detail.

According to one specific embodiment of the present invention, provided is a diol compound represented by the following Chemical Formula 1:

[Chemical Formula 1]

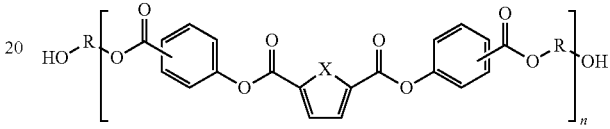

in Chemical Formula 1,

X is —O— or —S—,

R is $C_{6-60}$ arylene unsubstituted or substituted with $C_{1-10}$ alkyl, and n is an integer of 1 to 100.

The diol compound represented by Chemical Formula 1 has a novel modified structure including a 5-membered hetero ring group and carboxylates in the middle thereof and hydroxybenzoates at both ends thereof, and can function as a diol monomer compound in the polymerization of polycarbonate, and can have excellent impact resistance, transparency, heat resistance, etc., which are intrinsic properties of existing polycarbonate, while also exhibiting excellent weather resistance and hardness properties.

More specifically, the compound represented by Chemical Formula 1 has a structure in which hydroxybenzoates and a 5-membered hetero ring group are connected to each other via the carboxylate groups, and can exhibit excellent hardness, weather resistance, etc., as compared with existing polycarbonate, due to a structural change by fries-rearrangement of ester groups of the hydroxybenzoates, and the 5-membered hetero ring group. In addition, the effects of improving weather resistance and hardness of the polycarbonate can be further increased according to the number of (n) of the repeating units, the kind of hetero atom (X), and the ester linkage position of hydroxybenzoate, and different structures of the substituent R included in the structure of Chemical Formula 1.

As used herein, the alkyl group can be a linear or branched alkyl group having 1 to 10 carbon atoms or 1 to 5 carbon atoms. Specific examples of the alkyl group can include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, etc., but are not limited thereto.

As used herein, the cycloalkylene can be a monocyclic, polycyclic, or condensed cycloalkylene group having 3 to 20 carbon atoms or 3 to 15 carbon atoms. Specific examples of the cycloalkylene group include cyclopropane, cyclobutane, cyclopentane, cyclohexane, cycloheptane, cyclooctane, cyclodecane, etc., but are not limited thereto.

The arylene having 6 to 60 carbon atoms can be a monocyclic arylene or a polycyclic arylene. Specifically, the arylene having 6 to 60 carbon atoms can be a monocyclic or polycyclic arylene having 6 to 30 carbon atoms; or monocyclic or polycyclic arylene having 6 to 20 carbon atoms. More specifically, the arylene having 6 to 60 carbon atoms can include, as the monocyclic arylene, divalent residues derived from aromatic hydrocarbons, such as benzene, biphenyl, diphenylmethane, diphenylpropane, terphenyl, etc., and as the polycyclic arylene, divalent residues derived from aromatic hydrocarbons, such as naphthalene, anthracene, phenanthrene, triphenylene, pyrene, perylene, chrysene, fluorene, etc., but is not limited thereto. Further, the arylene having 6 to 60 carbon atoms can be substituted or unsubstituted with an alkyl group having 1 to 10 carbon atoms.

As used herein, the fluorene can be substituted, and two substituents can be connected to each other to form a spiro structure. When the fluorene is substituted, it can be

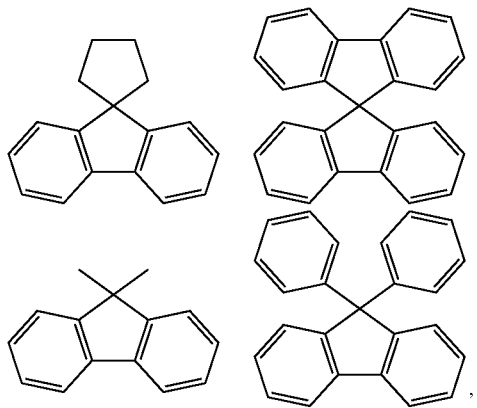

etc., but is not limited thereto.

As used herein, the heterocycloalkylene means that one or more of carbon atoms constituting the cycloalkylene group are substituted with one or more hetero atoms selected from the group consisting of N, O, P, Si, S, and combinations thereof.

According to one exemplary embodiment of the present invention, X in Chemical Formula 1 can be oxygen (—O—) or sulfur (—S—).

Further, in Chemical Formula 1, R can be

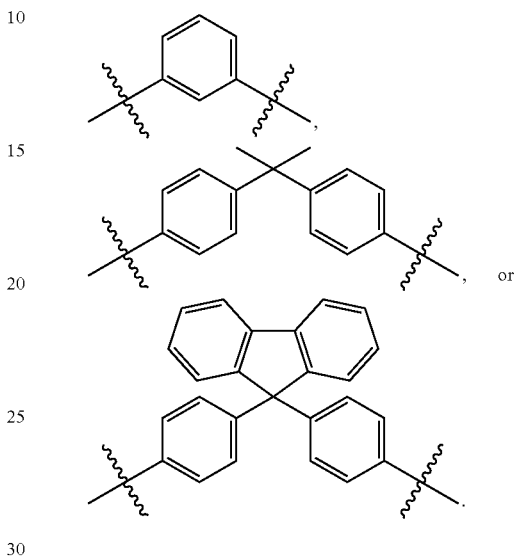

According to one exemplary embodiment of the present invention, considering the effect on the improvement of weather resistance and hardness of polycarbonate, n of Chemical Formula 1 can be an integer of 1 or more, or 2 or more, or 3 or more, or 5 or more, or 10 or more, or 14 or more, and 100 or less, or 50 or less, or 30 or less, or 20 or less, or 10 or less. Preferably, n of Chemical Formula 1 can be 2 to 10. When n is excessively large, solubility of the compound of Chemical Formula 1 is lowered, and thus productivity or processability of the polycarbonate may be poor.

According to one exemplary embodiment of the present invention, the diol compound represented by Chemical Formula 1 can be represented by the following Chemical Formula 1-1 to Chemical Formula 1-3:

[Chemical Formula 1-1]

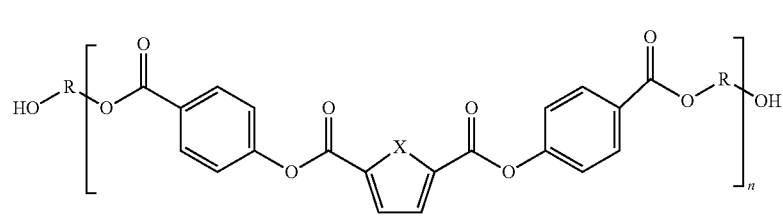

[Chemical Formula 1-2]

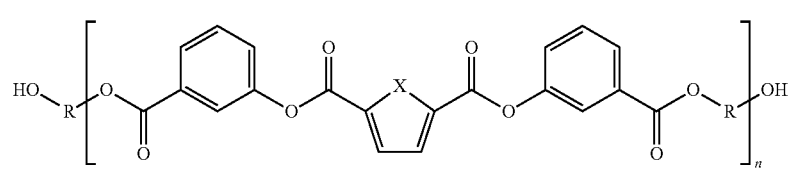

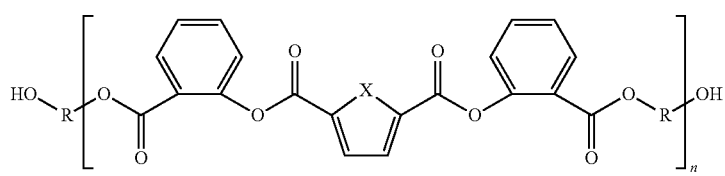

in Chemical Formulae 1-1 to 1-3,
X, R, and n are the same as defined in Chemical Formula 1.

According to one exemplary embodiment of the present invention, a weight average molecular weight (Mw) of the compound of Chemical Formula 1 can be appropriately controlled according to the purpose and use, and can be 500 g/mol or more, or 1,000 g/mol or more, or 1,500 g/mol or more, and 10,000 g/mol or less, or 5,000 g/mol or less, or 3,000 g/mol or less. In this regard, the weight average molecular weight can be obtained in terms of standard polystyrene (PS Standard) conversion value by gel permeation chromatography (GPC).

According to one exemplary embodiment of the present invention, the compound of Chemical Formula 1 can be used alone or in combination with another diol compound upon polymerization of the polycarbonate.

The compound of Chemical Formula 1 can be prepared according to a known method of preparing organic compounds, and for example, can be prepared according to the following Reaction Scheme 1. The method of preparing the compound of Chemical Formula 1 will be described in detail in Examples below.

[Chemical Formula 1]

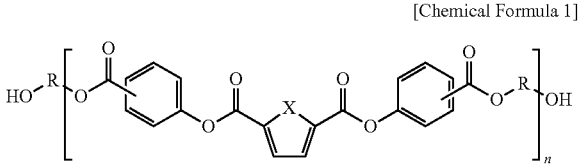

in Chemical Formula 1,
X is —O— or —S—,
R is $C_{6-60}$ arylene unsubstituted or substituted with $C_{1-10}$ alkyl, and
n is an integer of 1 to 100,

[Chemical Formula 2]

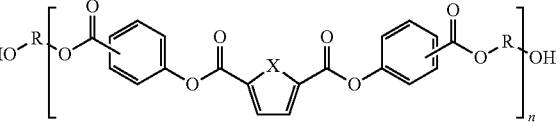

in Chemical Formula 2,
$R_1$ to $R_4$ are each independently hydrogen, $C_{1-10}$ alkyl, $C_{1-10}$ alkoxy, or halogen,
Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

Description of Chemical Formula 1 and specific exemplary compounds thereof are as described above.

[Reaction Scheme 1]

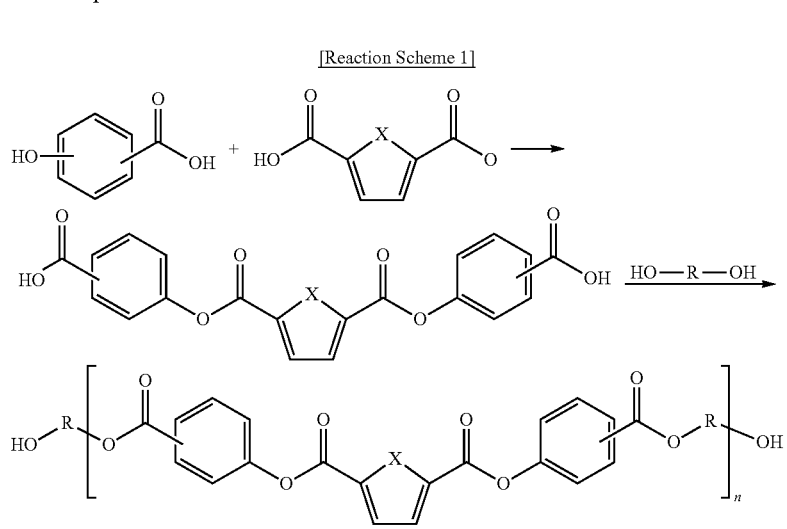

in Reaction Scheme 1, X, R, and n are the same as defined in Chemical Formula 1.

According to another exemplary embodiment of the present invention, provided is a polycarbonate including a diol compound represented by the following Chemical Formula 1, a compound represented by the following Chemical Formula 2, and a carbonate precursor-derived repeating unit:

According to one exemplary embodiment of the present invention, the compound represented by Chemical Formula 2 can be represented by the following Chemical Formula 2-1:

[Chemical Formula 2-1]

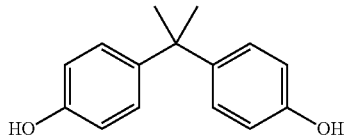

The polycarbonate of the present invention can be composed of only the repeating units derived from the compounds represented by Chemical Formula 1 and Chemical Formula 2, or can further include a repeating unit derived from another aromatic diol compound in addition thereto.

In Chemical Formula 2, $R_1$ to $R_4$ can be each independently hydrogen or $C_{1-4}$ alkyl. Alternatively, $R_1$ to $R_4$ can be each independently hydrogen, methyl, chloro, or bromo.

Further, in Chemical Formula 2, Z is each independently linear or branched $C_{1-10}$ alkylene unsubstituted or substituted with phenyl, and more preferably, methylene, ethane-1,1-diyl, propane-2,2-diyl, butane-2,2-diyl, 1-phenylethane-1,1-diyl, or diphenylmethylene.

The polycarbonate according to one exemplary embodiment of the present invention can include a repeating unit represented by the following Chemical Formula 3:

the repeating units derived from Chemical Formulae 1 and 2 can be controlled to prepare a polycarbonate having desired physical properties.

When the polycarbonate of the present invention includes the repeating unit derived from Chemical Formula 2 in addition to the repeating unit derived from Chemical Formula 1, a weight ratio thereof is not particularly limited, but for example, the weight ratio of the repeating unit derived from Chemical Formula 1 and the repeating unit derived from Chemical Formula 2 can be 5:95 to 50:50. In one specific exemplary embodiment, the weight ratio of the repeating unit derived from Chemical Formula 1 and the repeating unit derived from Chemical Formula 2 can be 5:95 to 50:50, or 10:90 to 40:60, or 10:90 to 30:70. When the weight ratio of the Chemical Formula 1 is too low, the polycarbonate may have insufficient hardness and weather resistance. On the contrary, when the weight ratio of the Chemical Formula 1 is too high, transparency or impact strength of the polycarbonate may decrease, or reactivity may decrease, and thus productivity of the polycarbonate may be decreased.

A weight average molecular weight (Mw) of the polycarbonate can be appropriately controlled according to the purpose and use, and can be 15,000 g/mol or more, or 20,000 g/mol or more, or 28,000 g/mol or more, and 70,000 g/mol or less, or 60,000 g/mol or less, or 50,000 g/mol or less, or 48,000 g/mol or less, or 47,000 g/mol or less. In this regard, the weight average molecular weight can be obtained in terms of standard polystyrene (PS Standard) conversion value by gel permeation chromatography (GPC).

[Chemical Formula 3]

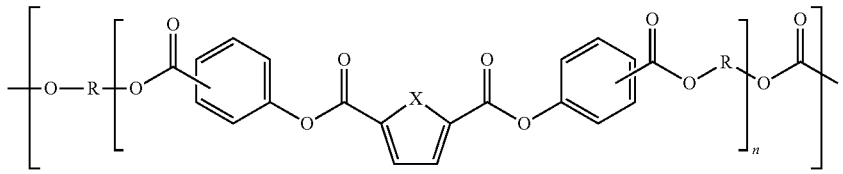

in Chemical Formula 3,

X, R, and n are the same as defined in Chemical Formula 1.

Further, the polycarbonate according to one exemplary embodiment of the present invention can include a repeating unit represented by the following Chemical Formula 4:

[Chemical Formula 4]

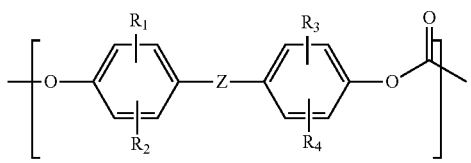

in Chemical Formula 4, $R_1$ to $R_4$, and Z are the same as defined in Chemical Formula 2.

The repeating unit derived from Chemical Formula 1 is characterized by having excellent hardness and weather resistance, and the repeating unit derived from Chemical Formula 2 is characterized by having excellent transparency, heat resistance, and impact resistance, and a weight ratio of Further, pencil hardness of the polycarbonate can exhibit high hardness of B or HB, as measured under a load of 1 kg at an angle of 45 degree in accordance with ASTM D3363.

Further, the polycarbonate of the present invention can have weather resistance (ΔE) of 11 or less, or 10 or less, or 9 or less, or 8 or less, or 7 or less, wherein the weather resistance (ΔE) is calculated from L', a' and b' values which are measured after measuring L, a, and b values in accordance with ASTM D7869, and then leaving the corresponding specimen under 2250 hr weather resistance condition using a Weather-Ometer® instrument. It is more preferred that the weather resistance is lower, and thus its lower limit is not particularly limited, but can be, for example, 1 or more, or 3 or more, or 4 or more.

Meanwhile, according to still another specific embodiment of the present invention, provided is a method of preparing the polycarbonate, the method including the step of polymerizing a composition including a compound represented by the following Chemical Formula 1, an aromatic diol compound represented by the following Chemical Formula 2, and a carbonate precursor:

[Chemical Formula 1]

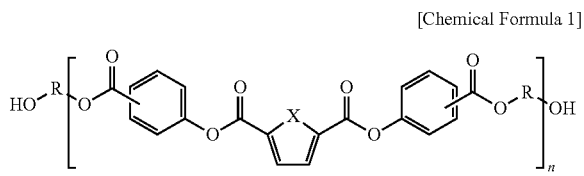

in Chemical Formula 1,
X is —O— or —S—,
R is $C_{6-60}$ arylene unsubstituted or substituted with $C_{1-10}$ alkyl, and
n is an integer of 1 to 100,

[Chemical Formula 2]

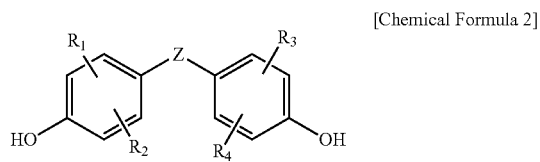

in Chemical Formula 2,
$R_1$ to $R_4$ are each independently hydrogen, $C_{1-10}$ alkyl, $C_{1-10}$ alkoxy, or halogen,
Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

Description of Chemical Formula 1 and specific exemplary compounds thereof are as described above.

Specific examples of the aromatic diol compound represented by Chemical Formula 2 can include one or more compounds selected from the group consisting of bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl)sulfide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane (bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, and 1,1-bis(4-hydroxyphenyl)-1-phenylethane.

Further, the carbonate precursor functions to connect the compound represented by Chemical Formula 1 and the compound represented by Chemical Formula 2, and specific examples thereof can include phosgene, triphosgene, diphosgene, bromophosgene, dimethyl carbonate, diethyl carbonate, dibutyl carbonate, dicyclohexyl carbonate, diphenyl carbonate, ditolyl carbonate, bis(chlorophenyl) carbonate, m-cresyl carbonate, dinaphthylcarbonate, bis(diphenyl) carbonate, or bishaloformate.

According to one specific embodiment, the method of polymerizing the polycarbonate using the composition including the aromatic diol compound represented by Chemical Formula 2 and the carbonate precursor in addition to the compound represented by Chemical Formula 1 can be used to perform a polymerization process at once on the composition including the above three precursor compounds.

In this regard, the compound represented by Chemical Formula 1 can be used in an amount of 1% by weight or more, 2% by weight or more, or 3% by weight or more, and 15% by weight or less, 12% by weight or less, or 10% by weight or less, with respect to 100% by weight of the composition.

Further, the aromatic diol compound represented by Chemical Formula 2 can be used in an amount of 40% by weight or more, 50% by weight or more, or 55% by weight or more, and 80% by weight or less, 75% by weight or less, or 70% by weight or less with respect to 100% by weight of the composition.

Further, the carbonate precursor can be used in an amount of 10% by weight or more, 15% by weight or more, or 20% by weight or more, and 50% by weight or less, 40% by weight or less, or 35% by weight or less with respect to 100% by weight of the composition.

In this regard, the polymerization can be performed by any method of interfacial polymerization or melt polymerization.

During the interfacial polymerization, it is preferred that the polymerization temperature is 0° C. to 40° C., and the reaction time is 10 min to 5 hr. Further, during the reaction, pH is preferably maintained at 9 or more, or 11 or more.

The solvent that can be used in the polymerization is not particularly limited as long as it is a solvent used in the art for the polymerization of polycarbonate. For example, halogenated hydrocarbons such as methylene chloride, chlorobenzene, etc. can be used.

In addition, the polymerization is preferably carried out in the presence of an acid binder, and as the acid binder, an alkali metal hydroxide such as sodium hydroxide, potassium hydroxide, etc., or an amine compound such as pyridine, etc. can be used.

Further, the polymerization is preferably performed in the presence of a molecular weight controller in order to control the molecular weight of polycarbonate during polymerization. As the molecular weight controller, $C_{1-20}$ alkylphenol can be used. Specific examples thereof can include p-tert-butylphenol, p-cumylphenol, decylphenol, dodecylphenol, tetradecylphenol, hexadecylphenol, octadecylphenol, eicosylphenol, docosylphenol, or triacontylphenol. The molecular weight controller can be injected before initiation of the polymerization, during initiation of the polymerization, or after initiation of the polymerization. The molecular weight controller can be used in an amount of 0.01 part by weight to 10 parts by weight, preferably 0.1 part by weight to 6 parts by weight, based on 100 parts by weight of the aromatic diol compound. Within this range, a desired molecular weight can be obtained.

To promote the polymerization reaction, a reaction promoter, for example, a tertiary amine compound such as triethylamine, tetra-n-butylammoniumbromide, tetra-n-butylphosphoniumbromide, etc., a quaternary ammonium compound, a quaternary phosphonium compound can be further used.

According to still another specific embodiment of the present invention, provided is a molded article manufactured by using the polycarbonate. As described above, the polycarbonate including the repeating unit derived from the compound represented by Chemical Formula 1 can have excellent mechanical properties while also having improved weather resistance, heat resistance, and transparency. Therefore, the molded article can be applied to a variety of fields, as compared with molded articles manufactured by using the existing polycarbonate. Further, the weight ratio of the repeating units derived from the compounds represented by Chemical Formulae 1 and 2 can be controlled to prepare a polycarbonate having desired physical properties.

The molded article can further include, if necessary, one or more selected from the group consisting of an antioxidant, a plasticizer, an antistatic agent, a nucleating agent, a flame retardant, a lubricant, an impact modifier, an optical brightener, an ultraviolet absorber, a pigment, and a dye, in addition to the polycarbonate according to the present invention.

A method of manufacturing the molded article can include, for example, the steps of mixing well the polycarbonate of the present invention and other additive using a mixer, extrusion-molding the mixture using an extruder to prepare a pellet, drying the pellet, and then injecting the pellet using an injection molding machine.

According to the present invention, provided are a novel structure of a polycarbonate having improved weather resistance, heat resistance, impact resistance, and hardness while having excellent mechanical properties, and a preparation method thereof.

DETAILED DESCRIPTION OF THE EMBODIMENTS

Figure 1:
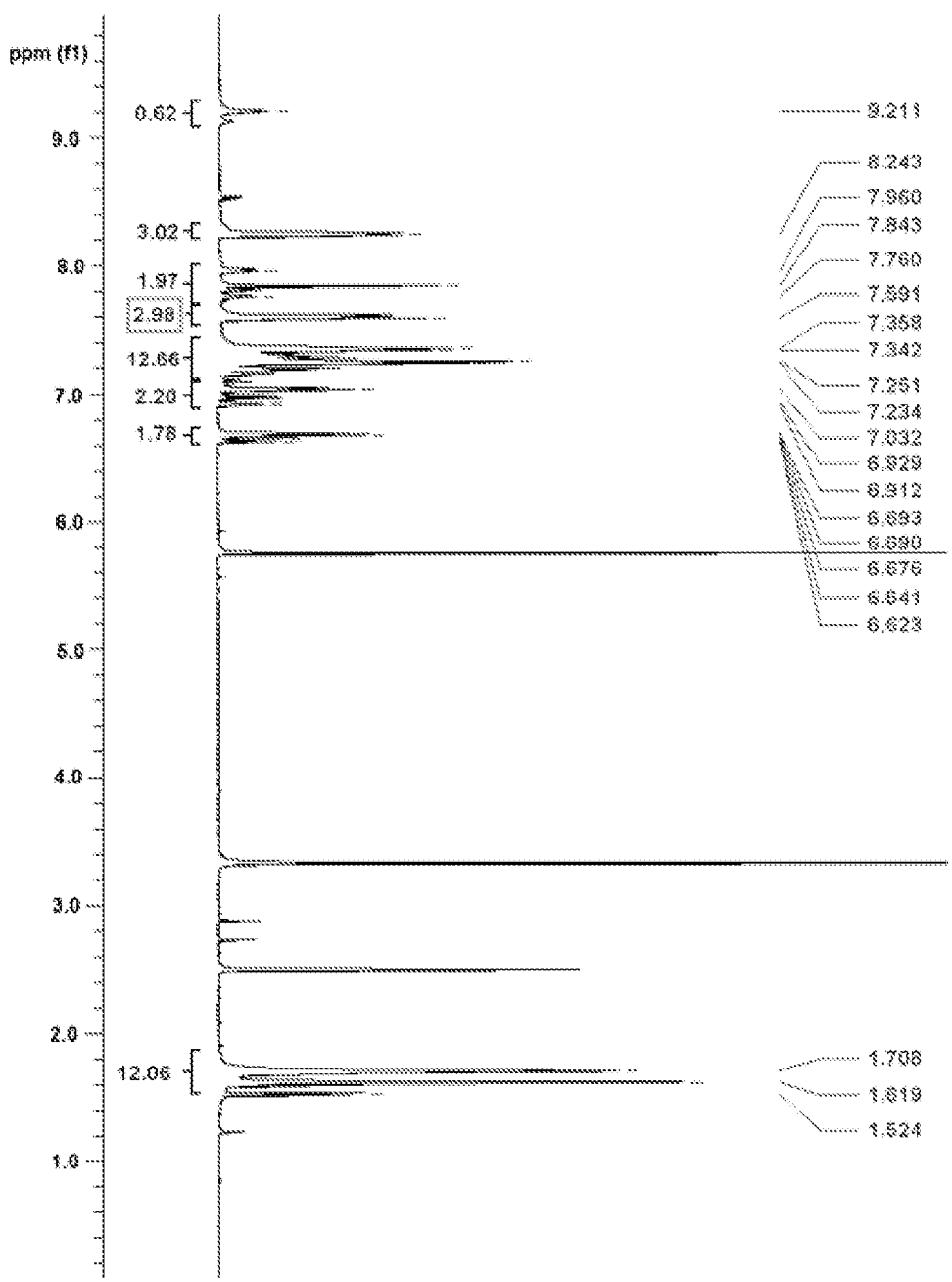
FIG. 1 shows a 1H-NMR graph of a compound prepared in Example 1.

The present invention will be described in more detail with reference to the following exemplary embodiments. However, the following exemplary embodiments are for illustrative purposes only, and the scope of the present invention is not intended to be limited by the following exemplary embodiments.

EXAMPLE

Example 1

(1) Preparation of bis(4-((4-(2-(4-hydroxyphenyl)propan-2-yl)phenoxy)carbonyl)phenyl) furan-2,5-dicarboxylate Furan-2,5-dicarboxylic acid (8 g) was placed in a 250-mL round bottom flask, dissolved in an MC solvent, and then oxalyl chloride (14.31 g) and DMF (0.3 mL) were added dropwise at room temperature, followed by stirring at room temperature for about 4 hours. When the reaction product became transparent, the solvent was removed using a rotary evaporator to obtain a chlorinated solid compound.

Thereafter, 4-hydroxybenzoic acid (21.23 g) was placed in a 500-mL round bottom flask, and dissolved in a 2 M NaOH aqueous solution (105 mL). A solution obtained by dissolving the previously obtained solid compound in tetrachloroethane solvent was added dropwise to the reaction flask for 1 hour using a dropping funnel. Thereafter, the mixture was further stirred for about 4 hours, and the reaction was terminated using a hydrochloric acid solution (35%). The resulting white solid was obtained through filtration under reduced pressure and washed with water and methaneol during filtration. The obtained solid was dried overnight in an oven at 60° C., and recrystallized several times with acetone to obtain a white dicarboxylic acid intermediate with a purity of 98%.

The dicarboxylic acid intermediate (10 g) was placed in a 250-mL round bottom flask, dissolved in an MC solvent, and oxalyl chloride (9.64 g) and DMF (0.2 g) were added dropwise at room temperature, followed by stirring at room temperature for about 4 hours. When the reaction product became transparent, the solvent was removed using a rotary evaporator to obtain a chlorinated solid compound.

In a separate 250-mL round flask, bisphenol A (11.81 g) was stirred in pyridine (7.98 g) and MC solvent. The previously completed compound without a separate purification process was slowly added to the bisphenol A solution prepared in the flask. After the addition, the reaction was allowed overnight at room temperature. After the reaction was completed, 1N—HCl was used to terminate the reaction, and after washing with Water/MC three times, the residual moisture in the organic layer was removed using $MgSO_4$, and the organic solvent was removed using a rotary evaporator. A yellow liquid final compound with viscosity (weight average molecular weight: 4,900 g/mol, n=8-9) was obtained in a final yield of 79%.

$^1$H-NMR (DMSO-$d_6$) of the compound is shown in FIG. 1.

(2) Preparation of Polycarbonate Resin 620 g of water, 112.46 g of bisphenol A, 14.09 g of bis(4-((4-(2-(4-hydroxyphenyl)propan-2-yl)phenoxy)carbonyl)phenyl) furan-2,5-dicarboxylate prepared in (1), 102.5 g of 40% by weight of NaOH, and 200 ml of $MeCl_2$ were added to a 2-L main reactor equipped with a nitrogen purge device and a condenser and enabling maintenance at room temperature using a circulator, followed by stirring for several minutes.

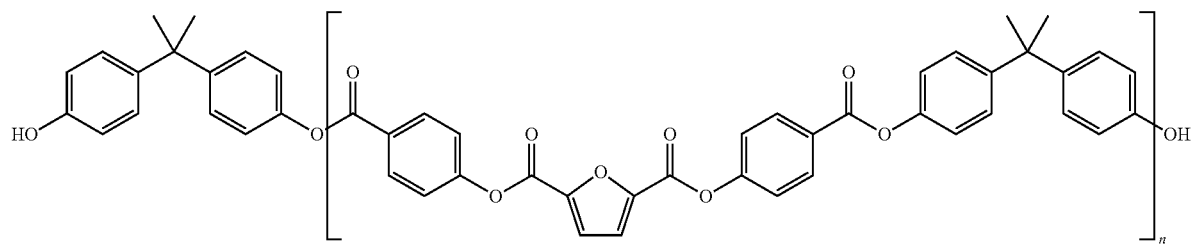

Nitrogen purging was stopped, 62.8 g of triphosgene and 120 ml of MeCl$_2$ were placed in a 1-L round bottom flask, triphosgene was dissolved therein, and the dissolved triphosgene solution was slowly added to the main reactor. After the addition was completed, 2.7 g of PTBP (p-tert-butylphenol) was added and stirred for 10 min. After stirring was completed, 99.8 g of 40% by weight of a NaOH aqueous solution was added, and 1.5 ml of TEA as a coupling agent was added. At this time, reaction pH was maintained at 11 to 13. After the reaction solution was allowed to stand for a time for sufficient reaction, pH was decreased to 3-4 by addition of HCl to complete the reaction. Then, stirring was stopped, the polymer layer was separated from the aqueous layer, the aqueous layer was removed, and the residue was washed with pure H$_2$O again, and this process was repeated a total of 3 to 5 times.

After the washing was completely carried out, only the polymer layer was extracted, and polymer crystals were obtained by re-precipitation using a non-solvent of methanol, H$_2$O, etc. In this regard, a weight average molecular weight of the prepared polycarbonate was 48,000 g/mol, in terms of PS standard.

Further, the results of NMR analysis confirmed that the repeating unit derived from the compound (1) was included in an amount of 10 wt %, based on the weight of the total repeating units.

Figure 2:
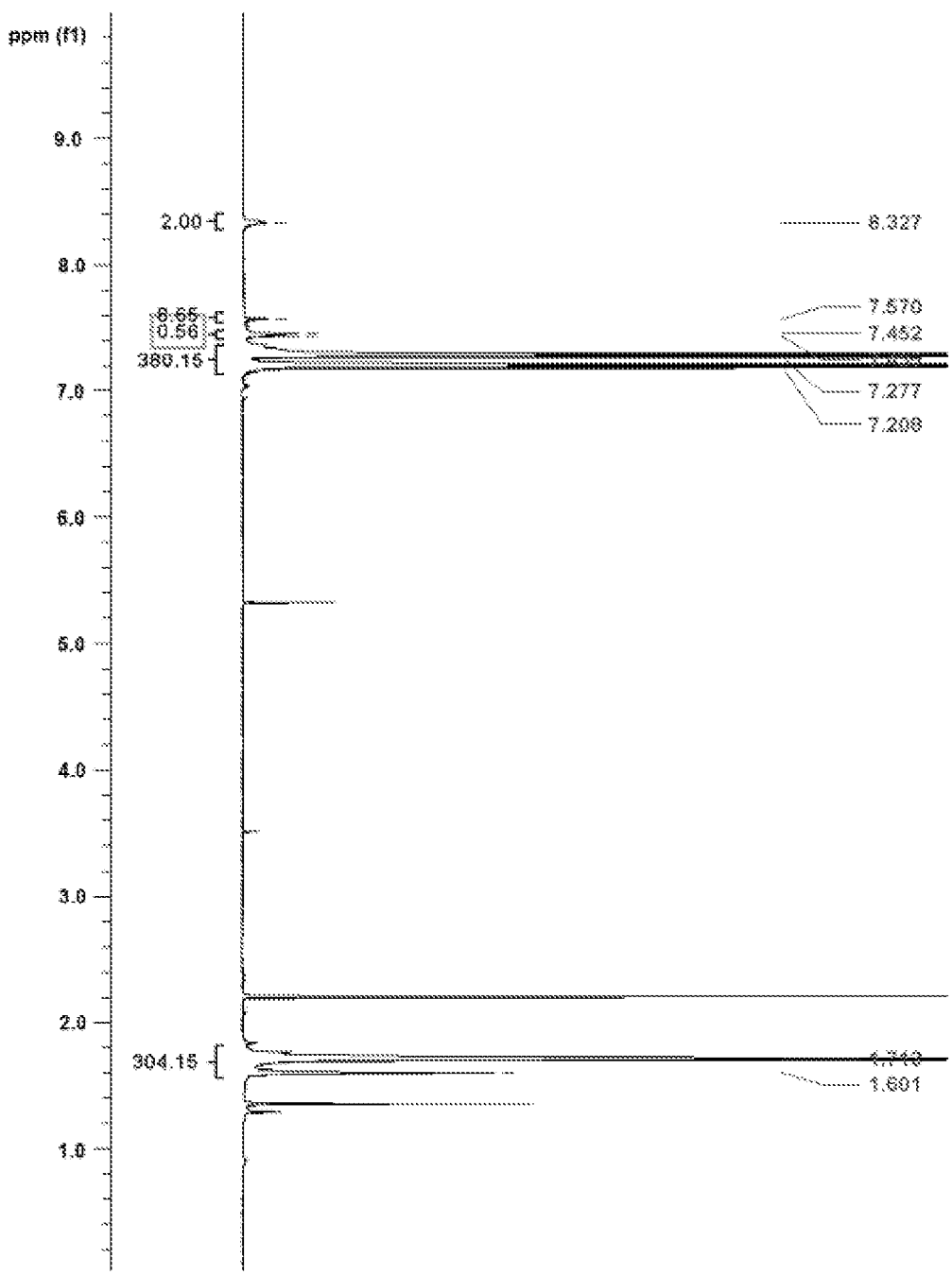
FIG. 2 shows a 1H-NMR graph of a copolycarbonate prepared in Example 1.

$^1$H-NMR (CDCl$_3$-d$_1$) of the compound is shown in FIG. 2.

Example 2

(1) Preparation of bis(4-((4-(2-(4-hydroxyphenyl)propan-2-yl)phenoxy)carbonyl)phenyl)thiophene-2,5-dicarboxylate

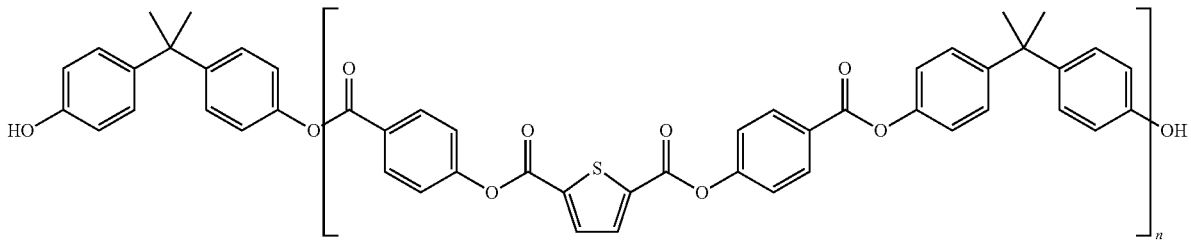

Synthesis was performed in the same manner as in (1) of Examples 1, except that 8.82 g of thiophene-2,5-dicarboxylic acid was used instead of 2,5-Furandicarboxylic acid of Example 1.

The final compound, bis(4-((4-(2-(4-hydroxyphenyl)propan-2-yl)phenoxy)carbonyl)phenyl)thiophene-2,5-dicarboxylate (weight average molecular weight: 3,500 g/mol, n=5~6) was obtained in a final yield of 72%.

Figure 3:
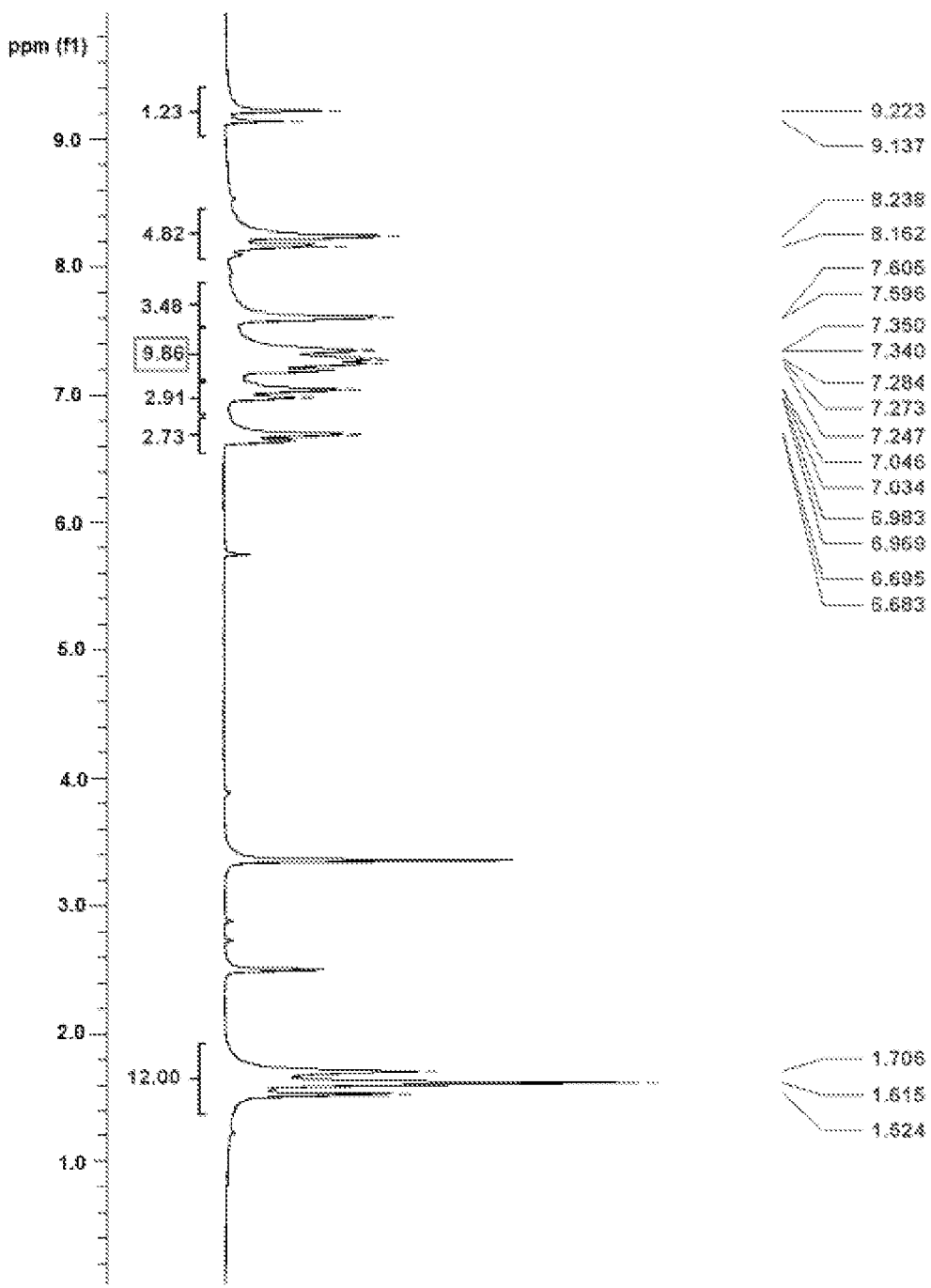
FIG. 3 shows a 1H-NMR graph of a compound prepared in Example 2.

$^1$H-NMR (DMSO-d$_6$) of the compound is shown in FIG. 3.

(2) Preparation of Polycarbonate Resin

A polycarbonate was prepared in the same manner as in the method of preparing a polycarbonate of Example 1, except that 14.03 g of bis(4-((4-(2-(4-hydroxyphenyl)propan-2-yl)phenoxy)carbonyl)phenyl)thiophene-2,5-dicarboxylate prepared in (1) was used instead of bis(4-((4-(2-(4-hydroxyphenyl)propan-2-yl)phenoxy)carbonyl)phenyl) furan-2,5-dicarboxylate of Example 1, and 112.55 g of bisphenol-A was used. In this regard, a weight average molecular weight of the prepared polycarbonate was 46,400 g/mol, in terms of PS standard. Further, the results of NMR analysis confirmed that the repeating unit derived from the compound (1) was included in an amount of 10 wt %, based on the weight of the total repeating units.

Figure 4:
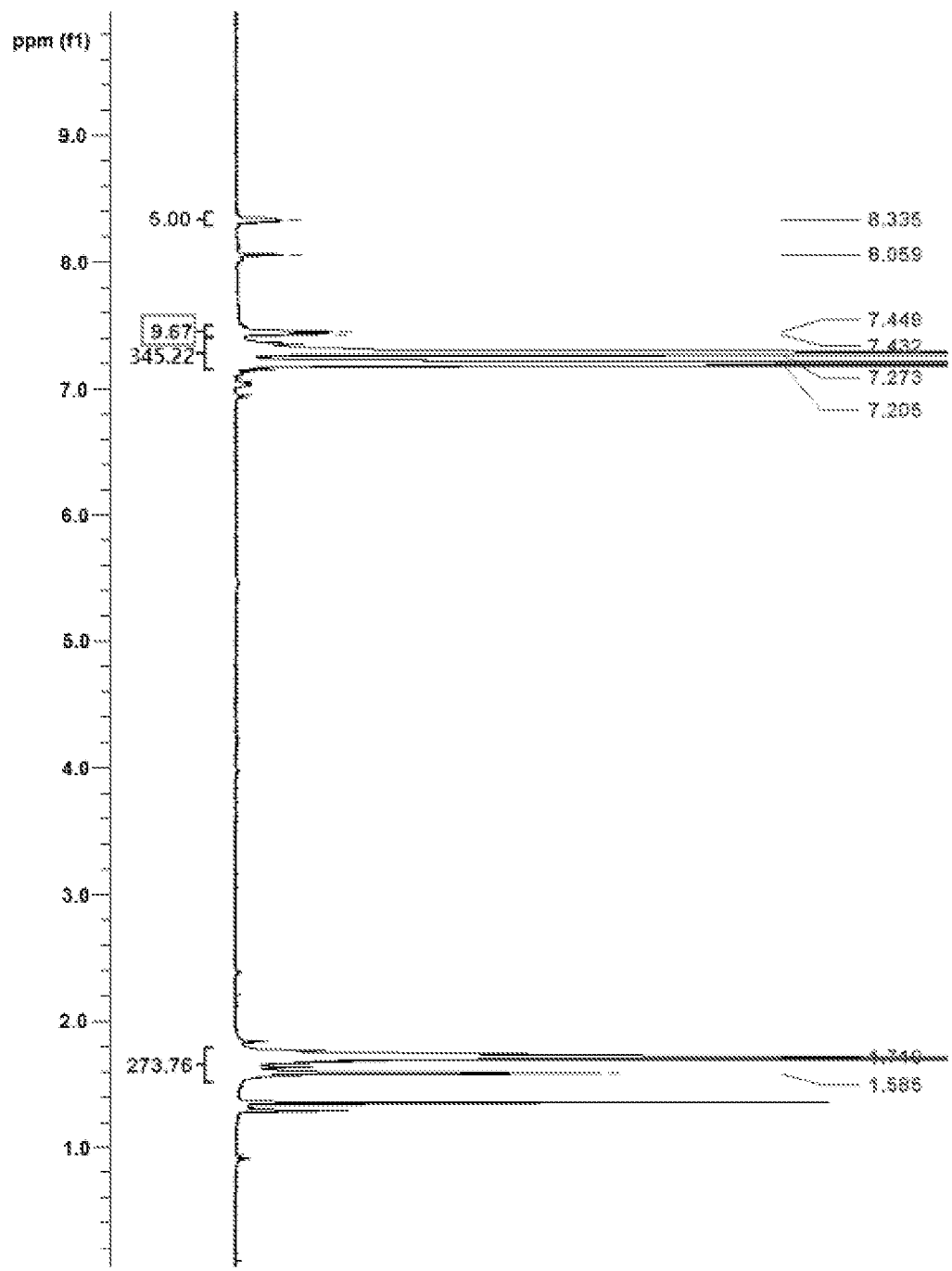
FIG. 4 shows a 1H-NMR graph of a copolycarbonate prepared in Example 2.

$^1$H-NMR (CDCl$_3$-d$_1$) of the compound is shown in FIG. 4.

Example 3

(1) Preparation of bis(4-((4-(2-(4-hydroxyphenyl)propan-2-yl)phenoxy)carbonyl)phenyl) furan-2,5-dicarboxylate

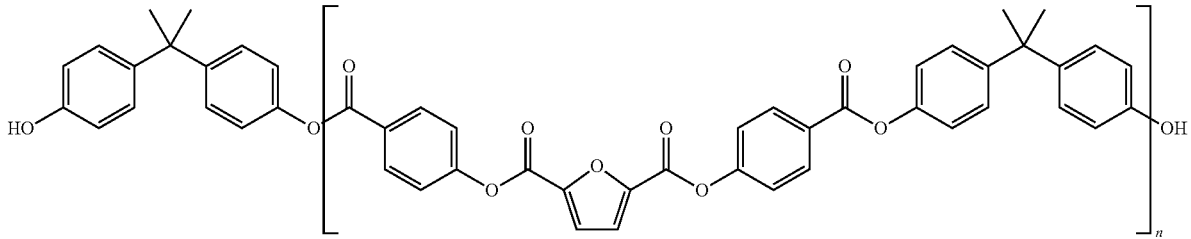

The same compound as in (1) of Example 1 was used.
(2) Preparation of Polycarbonate Resin A polycarbonate was prepared in the same manner as in the method of preparing a polycarbonate of Example 1, except that 6.74 g of bis(4-((4-(2-(4-hydroxyphenyl)propan-2-yl)phenoxy)carbonyl)phenyl) furan-2,5-dicarboxylate of Example 1 and 114.55 g of bisphenol-A were used. In this regard, a weight average molecular weight of the prepared polycarbonate was 45,200 g/mol, in terms of PS standard. Further, the results of NMR analysis confirmed that the repeating unit derived from the compound (1) was included in an amount of 5 wt %, based on the weight of the total repeating units.

Example 4

(1) Preparation of bis(4-((4-(2-(4-hydroxyphenyl)propan-2-yl)phenoxy)carbonyl)phenyl)thiophene-2,5-dicarboxylate

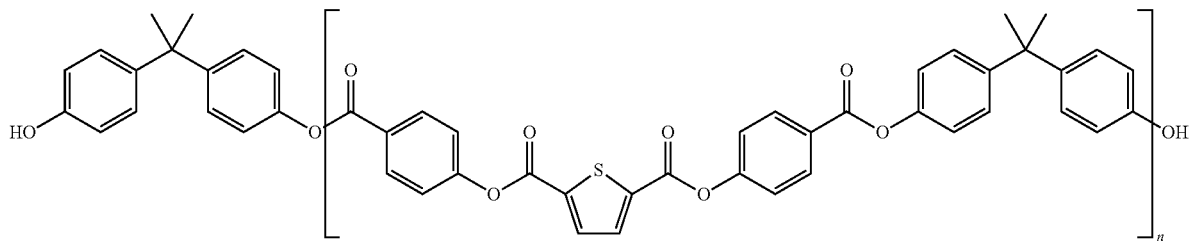

The same compound as in (1) of Example 2 was used.
(2) Preparation of Polycarbonate Resin A polycarbonate was prepared in the same manner as in the method of preparing a polycarbonate of Example 1, except that 6.75 g of bis(4-((4-(2-(4-hydroxyphenyl)propan-2-yl)phenoxy)carbonyl)phenyl)thiophene-2,5-dicarboxylate of Example 2 was used instead of bis(4-((4-(2-(4-hydroxyphenyl)propan-2-yl)phenoxy)carbonyl)phenyl) furan-2,5-dicarboxylate and 114.59 g of bisphenol-A was used. In this regard, a weight average molecular weight of the prepared polycarbonate was 47,800 g/mol, in terms of PS standard. Further, the results of NMR analysis confirmed that the repeating unit derived from the compound (1) was included in an amount of 5 wt %, based on the weight of the total repeating units.

Example 5

(1) Preparation of bis(4-((4-(2-(4-hydroxyphenyl)propan-2-yl)phenoxy)carbonyl)phenyl) furan-2,5-dicarboxylate

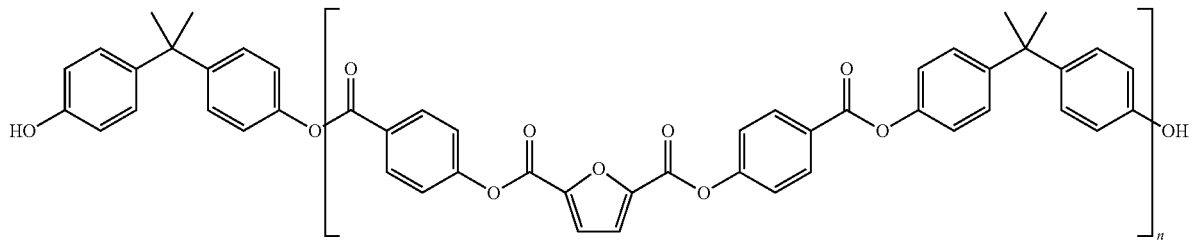

The same compound as in (1) of Example 1 was used.
(2) Preparation of Polycarbonate Resin A polycarbonate was prepared in the same manner as in the method of preparing a polycarbonate of Example 1, except that 30.43 g of bis(4-((4-(2-(4-hydroxyphenyl)propan-2-yl)phenoxy)carbonyl)phenyl) furan-2,5-dicarboxylate of Example 1 and 107.8 g of bisphenol-A were used. In this regard, a weight average molecular weight of the prepared polycarbonate was 49,500 g/mol, in terms of PS standard. Further, the results of NMR analysis confirmed that the repeating unit derived from the compound (1) was included in an amount of 20 wt %, based on the weight of the total repeating units.

Example 6

(1) Preparation of bis(4-((4-(2-(4-hydroxyphenyl)propan-2-yl)phenoxy)carbonyl)phenyl)thiophene-2,5-dicarboxylate

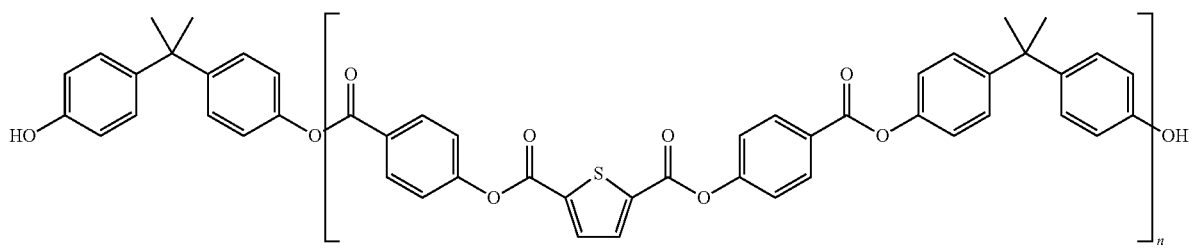

The same compound as in (1) of Example 2 was used.

(2) Preparation of Polycarbonate Resin

A polycarbonate was prepared in the same manner as in the method of preparing a polycarbonate of Example 1, except that 30.44 g of bis(4-((4-(2-(4-hydroxyphenyl)propan-2-yl)phenoxy)carbonyl)phenyl)thiophene-2,5-dicarboxylate of Example 2 was used instead of bis(4-((4-(2-(4-hydroxyphenyl)propan-2-yl)phenoxy)carbonyl)phenyl) furan-2,5-dicarboxylate of Example 1 and 107.96 g of bisphenol-A was used. In this regard, a weight average molecular weight of the prepared polycarbonate was 44,100 g/mol, in terms of PS standard. Further, the results of NMR analysis confirmed that the repeating unit derived from the compound (1) was included in an amount of 20 wt %, based on the weight of the total repeating units.

Example 7

(1) Preparation of bis(3-((4-(2-(4-hydroxyphenyl)propan-2-yl)phenoxy)carbonyl)phenyl) furan-2,5-dicarboxylate

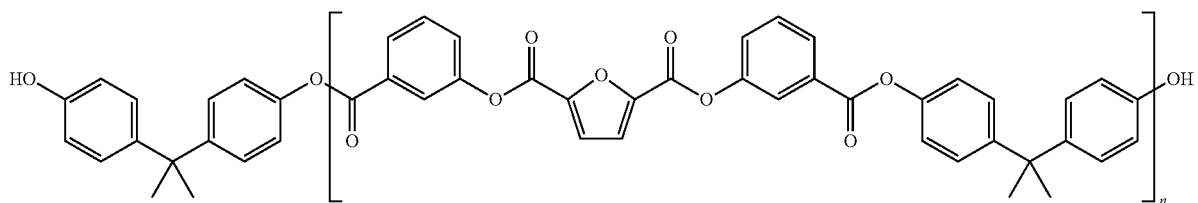

Synthesis was performed in the same manner as in (1) of Example 1, except that 3-hydroxybenzoic acid was used in an equal amount, instead of 4-hydroxybenzoic acid of Example 1. The final compound, bis(3-((4-(2-(4-hydroxyphenyl)propan-2-yl)phenoxy)carbonyl)phenyl) furan-2,5-dicarboxylate (weight average molecular weight: 3,500 g/mol, n=5-6) was obtained in a final yield of 80%.

Figure 5:
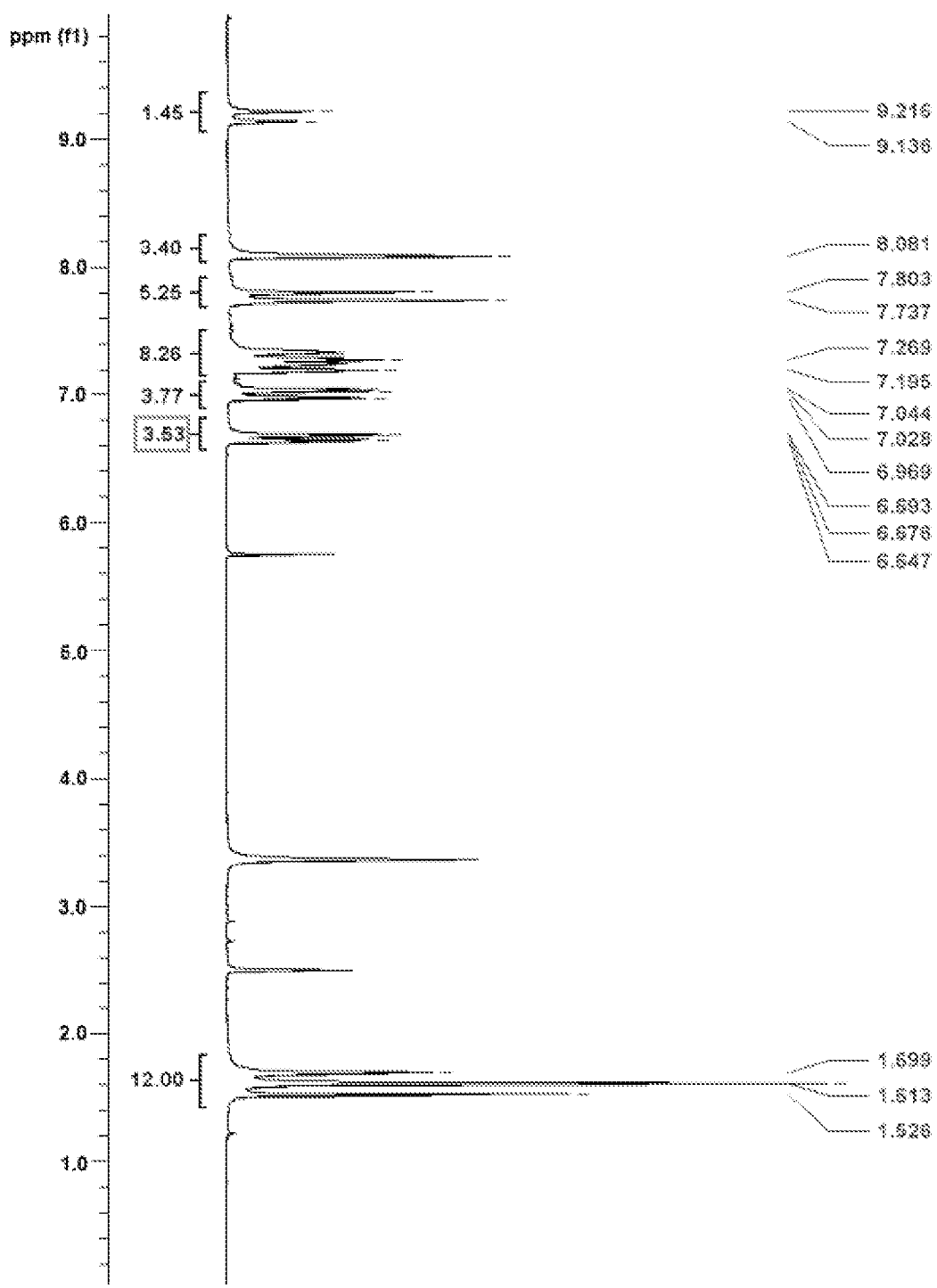
FIG. 5 shows a 1H-NMR graph of a compound prepared in Example 7.

$^1$H-NMR (DMSO-$d_6$) of the compound is shown in FIG. 5.

(2) Preparation of Polycarbonate Resin

A polycarbonate was prepared in the same manner as in the method of preparing a polycarbonate of Example 1, except that bis(3-((4-(2-(4-hydroxyphenyl)propan-2-yl)phenoxy)carbonyl)phenyl) furan-2,5-dicarboxylate prepared in Example 1 was used instead of bis(4-((4-(2-(4-hydroxyphenyl)propan-2-yl)phenoxy)carbonyl)phenyl) furan-2,5-dicarboxylate of Example 1. In this regard, a weight average molecular weight of the prepared polycarbonate was 47,200 g/mol, in terms of PS standard. Further, the results of NMR analysis confirmed that the repeating unit derived from the compound (1) was included in an amount of 10 wt %, based on the weight of the total repeating units.

Figure 6:
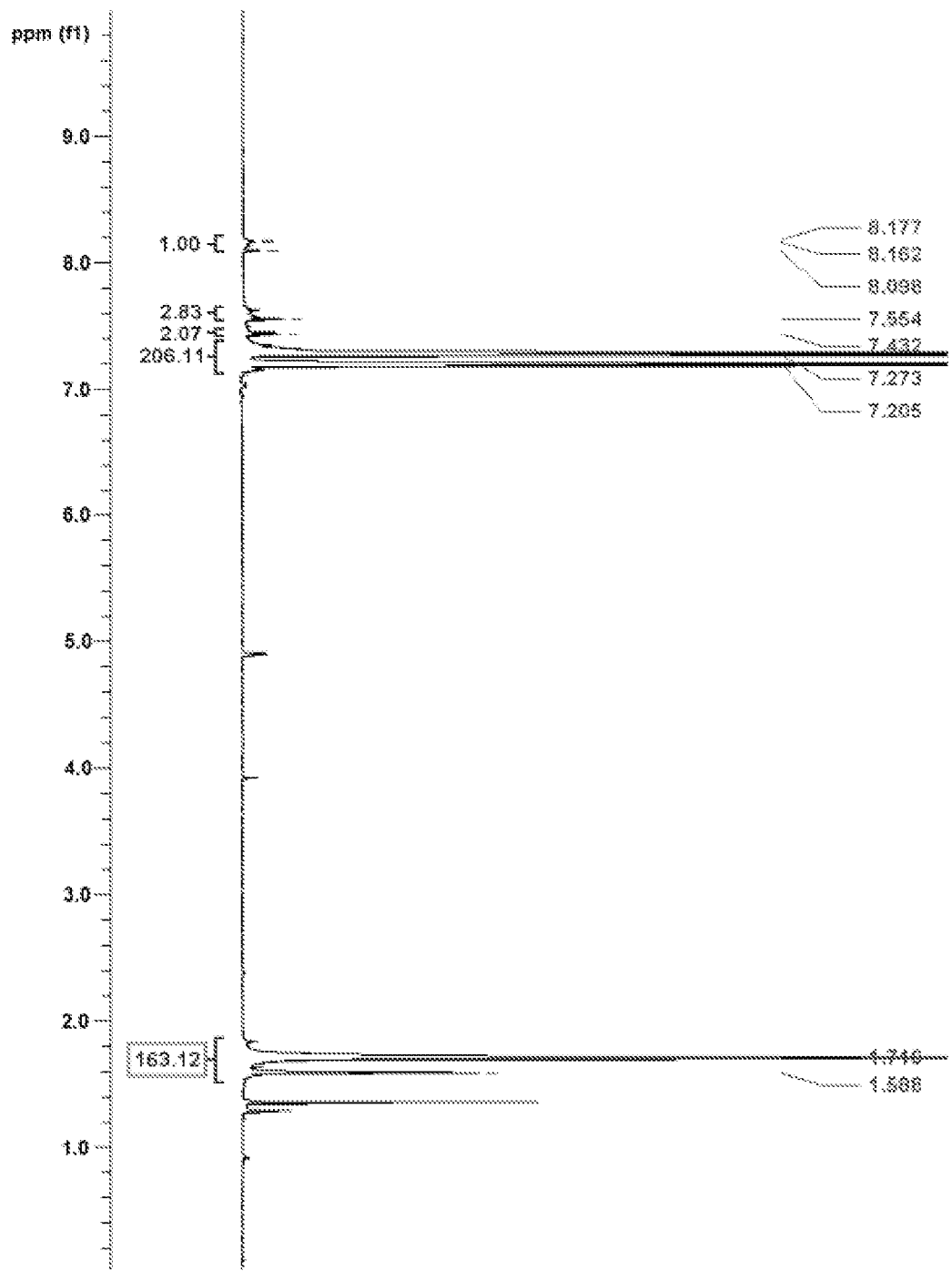
FIG. 6 shows a 1H-NMR graph of a copolycarbonate prepared in Example 7.

$^1$H-NMR (CDCl$_3$-$d_1$) of the compound is shown in FIG. 6.

Example 8

(1) Preparation of bis(3-((4-(2-(4-hydroxyphenyl)propan-2-yl)phenoxy)carbonyl)phenyl)thiophene-2,5-dicarboxylate

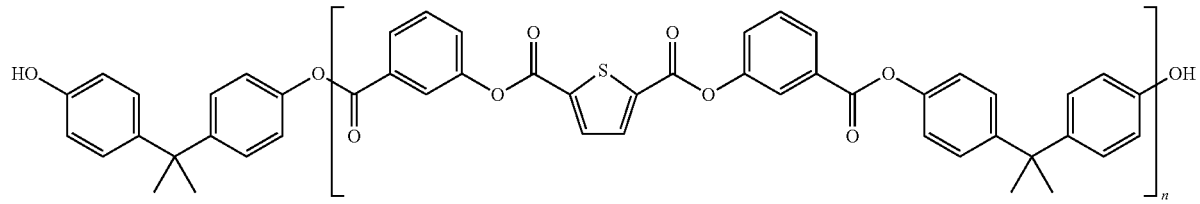

Synthesis was performed in the same manner as in (1) of Example 1, except that 3-hydroxybenzoic acid was used in an equal amount, instead of 4-hydroxybenzoic acid of Example 1, and 8.82 g of thiophene-2,5-dicarboxylic acid was used, instead of 2,5-Furandicarboxylic acid. The final compound, bis(3-((4-(2-(4-hydroxyphenyl)propan-2-yl)phenoxy)carbonyl)phenyl)thiophene-2,5-dicarboxylate (weight average molecular weight: 4,700 g/mol, n=7-8) was obtained in a final yield of 79%.

Figure 7:
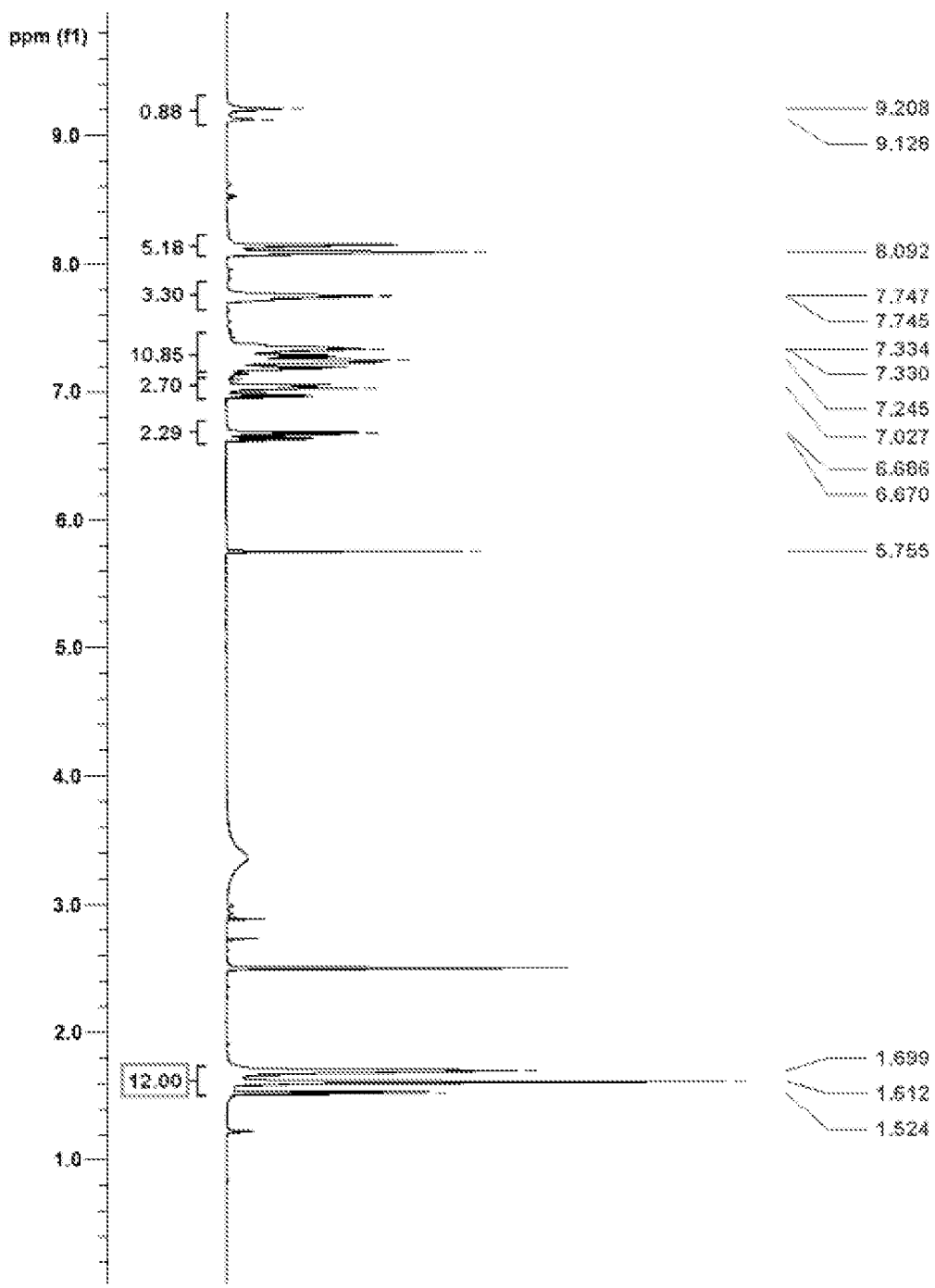
FIG. 7 shows a 1H-NMR graph of a compound prepared in Example 8.

$^1$H-NMR (DMSO-$d_6$) of the compound is shown in FIG. 7.

(2) Preparation of Polycarbonate Resin

A polycarbonate was prepared in the same manner as in the method of preparing a polycarbonate of Example 1, except that 14.03 g of bis(3-((4-(2-(4-hydroxyphenyl)propan-2-yl)phenoxy)carbonyl)phenyl)thiophene-2,5-dicarboxylate prepared in (1) was used instead of bis(4-((4-(2-(4-hydroxyphenyl)propan-2-yl)phenoxy)carbonyl)phenyl)furan-2,5-dicarboxylate of Example 1, and 112.55 g of bisphenol-A was used. In this regard, a weight average molecular weight of the prepared polycarbonate was 47,400 g/mol, in terms of PS standard. Further, the results of NMR analysis confirmed that the repeating unit derived from the compound (1) was included in an amount of 10 wt %, based on the weight of the total repeating units.

Figure 8:
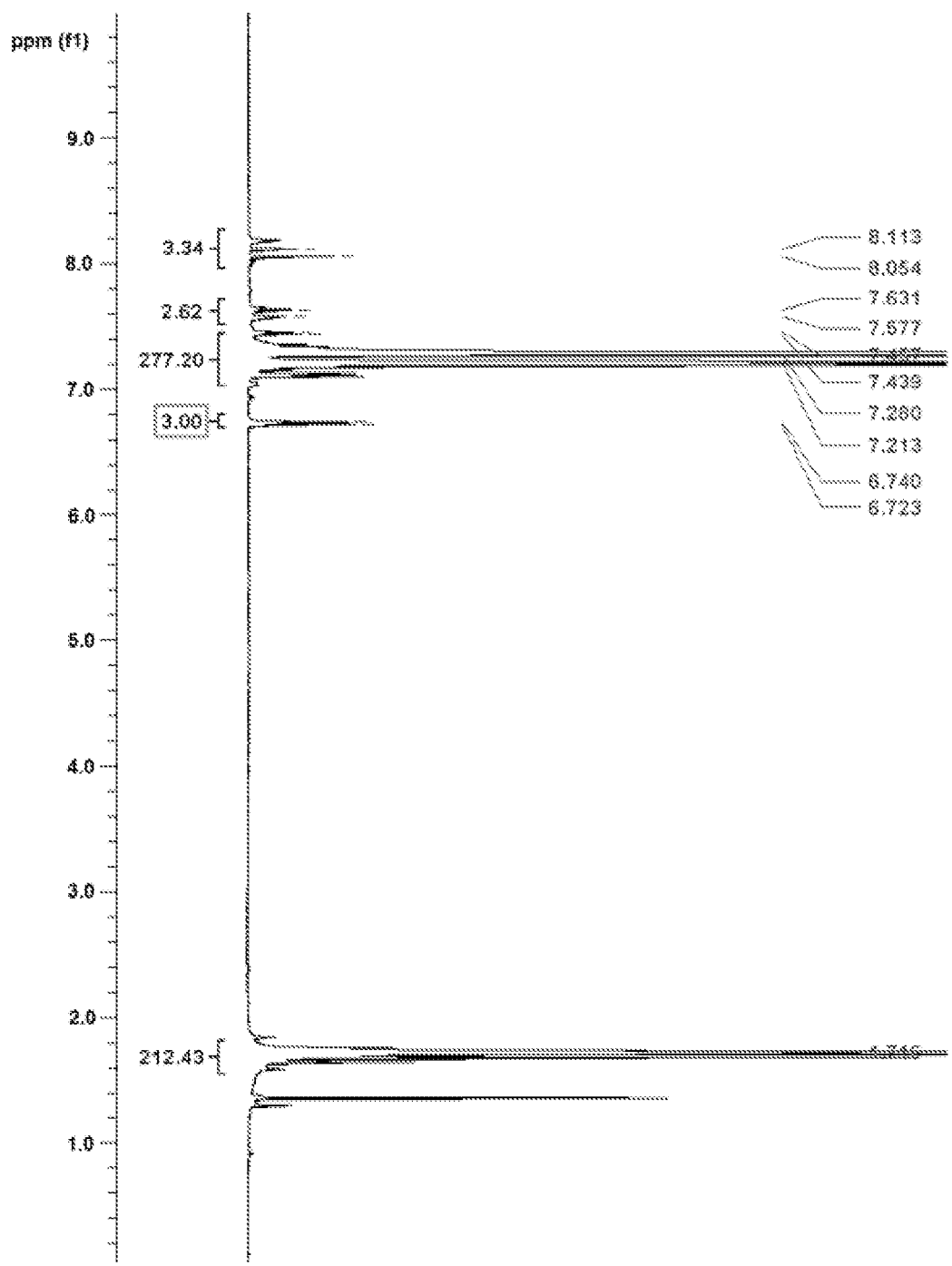
FIG. 8 shows a 1H-NMR graph of a copolycarbonate prepared in Example 8.

$^1$H-NMR (CDCl$_3$-$d_1$) of the compound is shown in FIG. 8.

Comparative Example 1

619 g of water, 116.5 g of bisphenol A, 102.5 g of 40% by weight of NaOH, and 195 ml of MeCl$_2$ were placed in a 2-L main reactor equipped with a nitrogen purge device and a condenser and enabling maintenance at room temperature using a circulator, followed by stirring for several minutes.

Nitrogen purging was stopped, 62.81 g of triphosgene and 120 ml of MeCl$_2$ were placed in a 1-L round bottom flask, triphosgene was dissolved therein, and the dissolved triphosgene solution was slowly added to the main reactor containing dissolved BPA. After the addition was completed, 2.7 g of PTBP (p-tert-butylphenol) was added and stirred for 10 min. After stirring was completed, 99.4 g of 40% by weight of a NaOH aqueous solution was added, and 1.04 g of TEA as a coupling agent was added. At this time, reaction pH was maintained at 11 to 13. After the reaction solution was allowed to stand for a time for sufficient reaction, pH was decreased to 3-4 by addition of HCl to complete the reaction. Then, stirring was stopped, the polymer layer was separated from the aqueous layer, the aqueous layer was removed, and the residue was washed with pure H$_2$O again, and this process was repeated a total of 3 to 5 times.

After the washing was completely carried out, only the polymer layer was extracted, and polymer crystals were obtained by re-precipitation using a non-solvent of methanol, H$_2$O, etc. In this regard, a weight average molecular weight of the prepared polycarbonate was 46,000 g/mol, in terms of PS standard.

Experimental Example: Evaluation of Physical Properties of Polycarbonate

Characteristics of injection specimens of the polycarbonates prepared in Examples and Comparative Examples were measured by the following methods, and the results are shown in Table 1.

Weight average molecular weight (g/mol): 200 mg of the polymer resin was diluted with 200 ml of a tetrahydrofuran (THF) solvent to prepare a sample of about 1000 ppm, of which molecular weight was measured using an Agilent 1200 series GPC system through an RI detector at a flow rate of 1 ml/min. To calculate the molecular weight of the sample, eight PS standards were used to prepare a calibration curve, and based on the curve, the molecular weight of the sample was determined.

Measurement of weather resistance (ΔE): L, a, and b values of a specimen having a thickness of ⅛ inch were measured in accordance with ASTM D7869 method, and the corresponding specimen was left under 2250 hr weather resistance condition in a Weather-Ometer® instrument, and then L', a' and b' values were measured again. Weather resistance ΔE was calculated therefrom according to the following Equation 1.

$$\Delta E = \sqrt{((L'-L)^2 + (a'-a)^2 + (b'-b)^2)}$$ [Equation 1]

Measurement of pencil hardness: In accordance with ASTM D3363, pencil was fixed at an angle of 45 degree in a pencil hardness tester, and pencil hardness was measured with pencils of 2B, B, and HB under a load of 1 kg.

Transparency: In accordance with ASTM D1003, transmittance was measured in the range of about 350 nm to 1050 nm using UltraScan PRO (manufactured by HunterLab).

Yellow Index (YI): In accordance with ASTM D1925, YI value was measured at room temperature (20° C.) using a UltraScan PRO (manufactured by HunterLab).

TABLE 1

| | Kind of repeating unit of Chemical Formula 1/ Weight ratio | Weight average molecular weight (g/mol) | Weather resistance (ΔE) | Pencil hardness | Transparency (%) | YI |
|---|---|---|---|---|---|---|
| Example 1 | Chemical Formula 1-1 (X=O), 10 wt % | 48,000 | 6.9 | B | 89.1 | 2.8 |
| Example 2 | Chemical Formula 1-1 (X=S), 10 wt % | 46,400 | 6.9 | B | 89.2 | 3.3 |
| Example 3 | Chemical Formula 1-1 (X=O), 5 wt % | 45,200 | 7.4 | B | 89.1 | 2.6 |
| Example 4 | Chemical Formula 1-1 (X=S), 5 wt % | 47,800 | 7.6 | B | 89.3 | 2.8 |
| Example 5 | Chemical Formula 1-1 (X=O), 20 wt % | 49,500 | 4.7 | HB | 89.2 | 3.0 |
| Example 6 | Chemical Formula 1-1 (X=S), 20 wt % | 44,100 | 5.2 | HB | 88.9 | 3.5 |
| Example 7 | Chemical Formula 1-2 (X=O), 10 wt % | 47,200 | 6.3 | HB | 89.2 | 3.1 |
| Example 8 | Chemical Formula 1-2 (X=S), 10 wt % | 47,400 | 6.6 | B | 89.0 | 3.4 |
| Comparative Example 1 | 100% BPA PC | 46,000 | 12 | 2B | 89.9 | 2.0 |

Referring to Table 1, the polycarbonates of all Examples including the repeating units of the present invention showed the effects of having remarkably improved weather resistance and pencil hardness while having similar transparency and yellow index, as compared with the general BPA polycarbonate of Comparative Example 1.

What is claimed is:

1. A polycarbonate comprising:
   a repeating unit derived from a diol compound represented by Chemical Formula 1;
   a repeating unit derived from a compound represented by Chemical Formula 2; and
   a carbonate precursor-derived repeating unit:

[Chemical Formula 1]

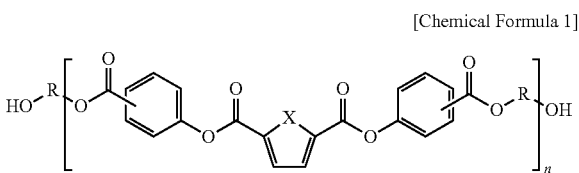

wherein, in Chemical Formula 1,
X is —O— or —S—,
R is $C_{6-60}$ arylene unsubstituted or substituted with $C_{1-10}$ alkyl, and
n is an integer of 1 to 100,

[Chemical Formula 2]

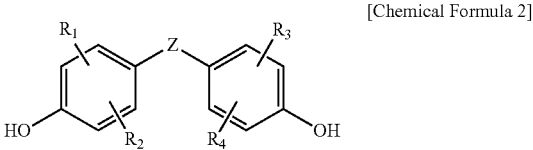

wherein, in Chemical Formula 2,
$R_1$ to $R_4$ are each independently hydrogen, $C_{1-10}$ alkyl, $C_{1-10}$ alkoxy, or halogen,
Z is $C_{1-10}$ alkylene unsubstituted or substituted with phenyl, $C_{3-15}$ cycloalkylene unsubstituted or substituted with $C_{1-10}$ alkyl, O, S, SO, $SO_2$, or CO.

2. The polycarbonate of claim 1, wherein the diol compound represented by Chemical Formula 1 is one of the compounds represented by Chemical Formula 1-1 to Chemical Formula 1-3:

[Chemical Formula 1-1]

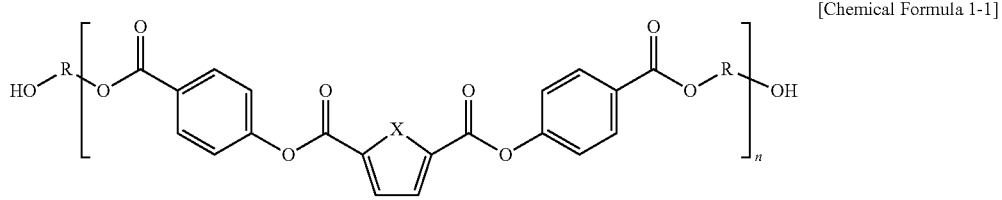

[Chemical Formula 1-2]

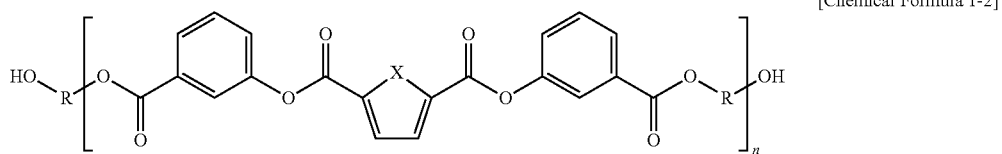

[Chemical Formula 1-3]

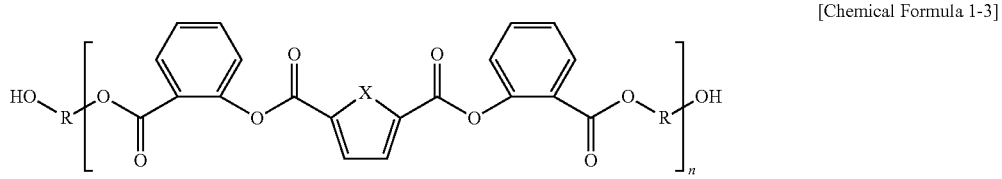

wherein, in Chemical Formulae 1-1 to 1-3,

X, R, and n are the same as defined in Chemical Formula 1.

3. The polycarbonate of claim 1, wherein $R_1$ to $R_4$ are each independently hydrogen or $C_{1-4}$ alkyl.

4. The polycarbonate of claim 1, wherein a weight ratio of a repeating unit derived from the compound represented by Chemical Formula 1 to a repeating unit derived from the compound represented by Chemical Formula 2 is 5:95 to 50:50.

5. The polycarbonate of claim 1, comprising a repeating unit represented by Chemical Formula 3:

[Chemical Formula 3]

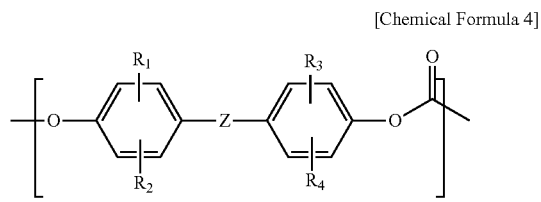

wherein, in Chemical Formula 3,

X, R, and n are the same as defined in Chemical Formula 1.

6. The polycarbonate of claim 1, comprising a repeating unit represented by Chemical Formula 4:

[Chemical Formula 4]

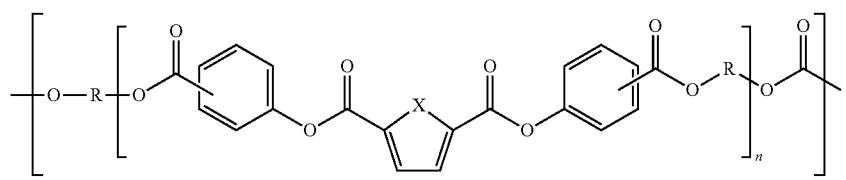

wherein, in Chemical Formula 4, $R_1$ to $R_4$, and Z are the same as defined in Chemical Formula 2.

7. The polycarbonate of claim 1, wherein pencil hardness of the polycarbonate is B or HB, as measured under a load of 1 kg at an angle of 45 degree in accordance with ASTM D3363.

8. The polycarbonate of claim 1, wherein weather resistance (ΔE value) measured according to Equation 1 is 1 to 11:

$$\Delta E=\sqrt{((L'-L)^2+(a'-a)^2+(b'-b)^2)}$$ [Equation 1]

wherein, in Equation 1,

L, a, and b are values of a specimen having a thickness of ⅛ inch, measured in accordance with ASTM D7869 method, and L', a' and b' are values measured again after leaving the corresponding specimen under 2250 hr weather resistance.

9. A method of preparing a polycarbonate, the method comprising a step of:

polymerizing a composition including a diol compound represented by Chemical Formula 1, an aromatic diol compound represented by Chemical Formula 2, and a carbonate precursor:

[Chemical Formula 1]

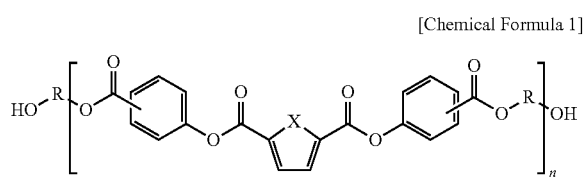

wherein, in Chemical Formula 1,

X is —O— or —S—,

R is $C_{6-60}$ arylene unsubstituted or substituted with $C_{1-10}$ alkyl, and n is an integer of 1 to 100,

[Chemical Formula 2]

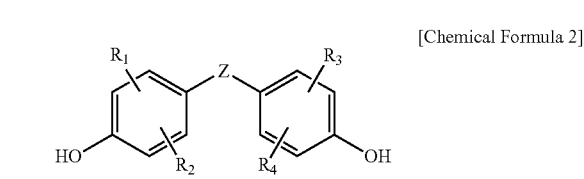

wherein, in Chemical Formula 2, $R_1$ to $R_4$ are each independently hydrogen, $C_{1-10}$ alkyl, $C_{1-10}$ alkoxy, or halogen, and Z is $C_{1-10}$ alkylene unsubstituted or substituted with phenyl, $C_{3-15}$ cycloalkylene or substituted with $C_{1-10}$ alkyl, O, S, SO, $SO_2$, or CO.

10. The method of claim 9, wherein the diol compound represented by Chemical Formula 1 is one of the compounds represented by Chemical Formula 1-1 to Chemical Formula 1-3:

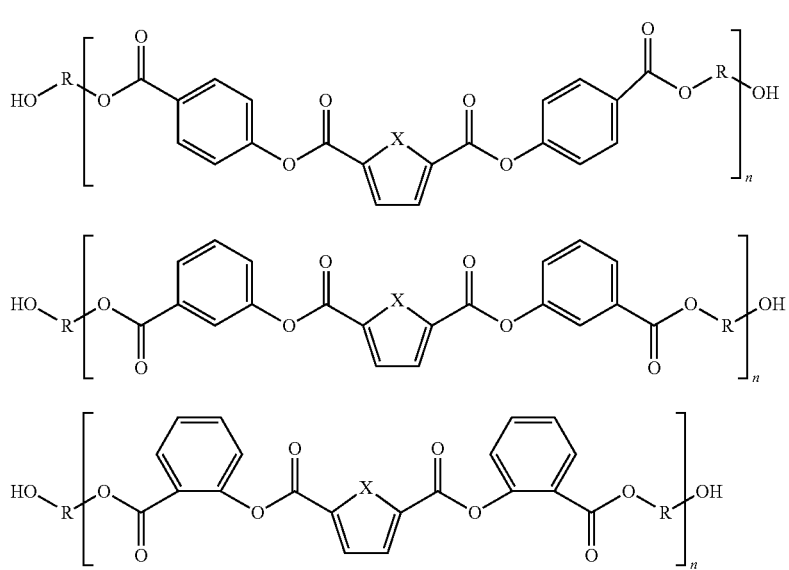

[Chemical Formula 1-1]

[Chemical Formula 1-2]

[Chemical Formula 1-3]

wherein, in Chemical Formulae 1-1 to 1-3,

X, R, and n are the same as defined in Chemical Formula 1.

11. The method of claim 9, wherein the aromatic diol compound represented by Chemical Formula 2 is one or more compounds selected from the group consisting of bis(4-hydroxyphenyl) methane, bis(4-hydroxyphenyl) ether, bis(4-hydroxyphenyl) sulfone, bis(4-hydroxyphenyl) sulfoxide, bis(4-hydroxyphenyl) sulfide, bis(4-hydroxyphenyl) ketone, 1,1-bis(4-hydroxyphenyl) ethane, 2,2-bis(4-hydroxyphenyl) propane (bisphenol A), 2,2-bis(4-hydroxyphenyl) butane, 1,1-bis(4-hydroxyphenyl)cyclohexane (bisphenol Z), 2,2-bis(4-hydroxy-3,5-dibromophenyl) propane, 2,2-bis(4-hydroxy-3,5-dichlorophenyl) propane, 2,2-bis(4-hydroxy-3-bromophenyl) propane, 2,2-bis(4-hydroxy-3-chlorophenyl) propane, 2,2-bis(4-hydroxy-3-methylphenyl) propane, 2,2-bis(4-hydroxy-3,5-dimethylphenyl) propane, and 1,1-bis(4-hydroxyphenyl)-1-phenylethane.

12. A molded article comprising the polycarbonate of claim 1.

* * * * *